(12) United States Patent
Stelter et al.

(10) Patent No.: US 6,296,800 B1
(45) Date of Patent: Oct. 2, 2001

(54) METHOD FOR THE MANUFACTURE OF BREAST PROSTHESES

(75) Inventors: Nils Stelter, Achenmuehle; Hans Stuffer, Nussdorf/Inn, both of (DE)

(73) Assignee: Amoena Medizin-Orthopädie-Technik GmbH & Co., Raubling (DE)

(*) Notice: Subject to any disclaimer, the term of this patent is extended or adjusted under 35 U.S.C. 154(b) by 0 days.

(21) Appl. No.: 09/621,538

(22) Filed: Jul. 21, 2000

(30) Foreign Application Priority Data

Jul. 28, 1999 (DE) .............................. 199 35 494

(51) Int. Cl.[7] ...................................... B29C 35/02
(52) U.S. Cl. .................... 264/267; 264/46.6; 264/320; 264/DIG. 6
(58) Field of Search ..................... 264/267, 320, 264/DIG. 6, 46.6

(56) References Cited

U.S. PATENT DOCUMENTS

| | | | |
|---|---|---|---|
| 4,250,136 | * | 2/1981 | Rex ...................................... 264/257 |
| 4,380,569 | * | 4/1983 | Shaw ............................... 264/DIG. 6 |
| 4,955,907 | * | 9/1990 | Ledergerber .............................. 623/8 |
| 5,549,671 | * | 8/1996 | Waybright et al. ....................... 623/8 |
| 5,738,812 | * | 4/1998 | Wild ...................................... 264/267 |

FOREIGN PATENT DOCUMENTS

| | | |
|---|---|---|
| 92 01 918 | 7/1992 | (DE) . |
| 44 13 076 | 10/1995 | (DE) . |
| 295 19 283 | 4/1996 | (DE) . |
| 295 16 281 | 3/1997 | (DE) . |
| 197 54 144 | 11/1998 | (DE) . |
| 2 021 954 | * 12/1979 | (GB) . |

* cited by examiner

*Primary Examiner*—Allan R. Kuhns
(74) *Attorney, Agent, or Firm*—Jacobson Holman, PLLC

(57) ABSTRACT

For the manufacture of breast prostheses consisting of a shell-shaped body made from an addition-vulcanising two-components silicone rubber mass, which body is contained in plastic films enveloping it, a filler of low density consisting of hollow spheres or microspheres is added to the two-component silicone rubber mass, said mixture is poured into a sheath of plastic films and cured in a mould under the effect of heat. To achieve the best possible processing capability of the mixture of the two-component silicone rubber mass with the hollow spheres or microspheres, the hollow spheres or microspheres are plastically deformed before they are mixed with the two components of the silicone rubber mass.

3 Claims, No Drawings

METHOD FOR THE MANUFACTURE OF BREAST PROSTHESES

The invention relates to a method for the manufacture of breast prostheses consisting of a shell-shaped body made from an addition-vulcanising two-components silicone rubber mass, which body is contained in plastic films enveloping it, where a filler of low density consisting of hollow spheres or microspheres is added to the two-component silicone rubber mass, the mixture is poured into a sheath of plastic films and cured in a mould under the effect of heat.

Breast prostheses of this type are known from DE 92 01 918 U. Such breast prostheses are manufactured using the conventional method, in which the two components of the silicone rubber are set with regard to their viscosity so that they can be pumped together with the filler and guided through a mixer to fill the plastic films already welded together to prosthesis sheaths. To be pumpable, the two components or the mixture must have a relatively low viscosity which leads to the lighter filler spheres, which have a density of <0.1 g/cm$^3$, floating in the pouch-shaped plastic sheaths inserted in the mould before their curing so that the uniform distribution of the filler in the silicone rubber mass is lost and the filler migrates from the lower regions of the mixture to the top and collects in the upper region of the pouch-shaped plastic sheaths.

Further problems with the processing of the mixture of the two-component silicone rubber with the filler spheres arise in particular during the pumping of said mixture. The fillers consisting of the hollow spheres or microspheres form a compressible component in the mixture so that the total mixture no longer behaves like a liquid, but can lead to different volume discharges as the result of pressure differences in the pump operation. This is particularly problematic when filling the plastic films welded together into the prosthesis sheaths.

Various proposals are known from DE 44 13 076 A1 which are intended to prevent the problem of the unwanted floating of the filler spheres or microspheres. However, these proposals do not lead to a remedy for the problems in the processing of the mixture of hollow spheres or microspheres with the still unvulcanised two-component silicone rubber mass.

It is therefore the object of the invention to further develop a generic method in such a way that with a uniform distribution of the filler in the prosthesis body, a simpler and more reliable processing capability of the materials used is made possible during the manufacturing method.

This object is solved in accordance with the invention starting from generic methods by the additional features of the characterising part of claim 1. In accordance with this solution in accordance with the invention, the hollow spheres or the microspheres are plastically deformed before they are mixed with at least one of the two components of the silicone rubber mass.

In accordance with an advantageous aspect of the invention, the volume of the hollow spheres or microspheres is reduced by deformation under pressure or by mechanical strain. Ideally, the volume is lowered by around ⅓ of the starting volume. The ideal volume reduction depends, however, on the properties of the microspheres or hollow spheres used. Due to the compression of these microspheres or hollow spheres, their compressibility is almost completely eliminated so that the mixture of the two-component silicone rubber mass with the hollow spheres or microspheres can be processed almost like a liquid. In particular the pressure differences occurring during pump operation no longer lead to the different volume discharges which led time and time again to dosing problems, especially during the filling of the prosthesis sheath. All in all, the handling of the mixture can be substantially improved. A particularly advantageous effect also consists of the floating tendency of the hollow spheres or microspheres being able to be substantially reduced.

To manufacture these light prostheses in accordance with the invention, the filler comprising the hollow spheres and the microspheres is added to one or preferably both components of the silicone rubber mass and mixed into the components. A uniform mixture is achieved by a mixing process in a static or dynamic mixer, whereby the hollow spheres or microspheres previously deformed, for example, mechanically in a mixer can be mixed well into the two components of the silicone rubber mass without any segregation tendency. Subsequently, this mixture is poured into the prepared plastic sheath consisting of two welded films. The plastic sheath filled in this way is then inserted in a mould in the conventional manner and cured therein with heat being applied. During the curing process under heat, the hollow spheres or microspheres expand again with their volumes increasing. Due to the effect of heat, the plastic sheath becomes soft and plastically formable on the one hand, and, on the other hand, the gas inside the hollow spheres or microspheres expands and leads to their compressed plastic sheath again assuming the original spherical shape. The now re-expanding hollow spheres or microspheres can no longer float due to the already advanced vulcanisation condition in the thus now increased viscosity within the two-component silicone rubber mass. It is rather the case that they are bound in the vulcanising silicone rubber mass. The pouring opening can be welded in a known manner after filling or during curing.

What is claimed is:

1. A method for the manufacture of breast prostheses consisting of a shell-shaped body made from an addition-vulcanising two-component silicone rubber mass, which body is contained in plastic films enveloping it, where a filler of low density consisting of hollow spheres or microspheres is added to the two-component silicone rubber mass, the mixture is poured into a sheath of plastic films and cured in a mould under the effect of heat, characterised in that
the hollow spheres or microspheres are plastically deformed before they are mixed with at least one of the two components of the silicone rubber mass.

2. A method in accordance with claim 1, wherein the volume of the hollow spheres or microspheres is reduced by deformation under pressure or by mechanical strain.

3. A method in accordance with claim 1, wherein the volume of the hollow spheres or microspheres is reduced by up to around ⅓ of the starting volume.

* * * * *